(12) United States Patent
Rosa et al.

(10) Patent No.: US 8,293,218 B2
(45) Date of Patent: Oct. 23, 2012

(54) SKIN CARE COMPOSITIONS COMPRISING SUBSTITUTED MONOAMINES

(75) Inventors: Jose Guillermo Rosa, Shelton, CT (US); Bijan Harichian, Brookfield, CT (US); Diana Jean Drennan, Naugatuck, CT (US); John Steven Bajor, Cheshire, CT (US); Carol Annette Bosko, Newtown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 145 days.

(21) Appl. No.: 12/845,814

(22) Filed: Jul. 29, 2010

(65) Prior Publication Data

US 2012/0027699 A1 Feb. 2, 2012

(51) Int. Cl.
*A61Q 19/02* (2006.01)
*A61K 8/00* (2006.01)
*A61K 8/41* (2006.01)
*A61K 31/137* (2006.01)

(52) U.S. Cl. ............... 424/62; 424/401; 514/654
(58) Field of Classification Search .......... 424/62, 424/401; 514/654
See application file for complete search history.

(56) References Cited

U.S. PATENT DOCUMENTS

| | | | |
|---|---|---|---|
| 4,412,943 A | 11/1983 | Hirota et al. | 252/546 |
| 5,393,519 A | 2/1995 | Dowell et al. | 424/70.11 |
| 6,699,873 B1 | 3/2004 | Maguire | |
| 2001/0002253 A1* | 5/2001 | Farer et al. | 424/61 |
| 2001/0041170 A1 | 11/2001 | Winchell et al. | 424/65 |
| 2003/0172471 A1 | 9/2003 | Chassot et al. | 8/405 |
| 2004/0082779 A1 | 4/2004 | Vos et al. | |
| 2005/0152859 A1 | 7/2005 | Dooley et al. | |
| 2005/0220832 A1 | 10/2005 | Walton | 424/401 |
| 2008/0019927 A1* | 1/2008 | Zhang et al. | 424/45 |
| 2009/0010860 A1 | 1/2009 | Wagner et al. | 424/59 |

FOREIGN PATENT DOCUMENTS

| | | |
|---|---|---|
| DE | 22860 | 3/1962 |
| EP | 0 653 208 | 5/1995 |
| EP | 820763 A2 | 1/1998 |
| EP | 0 922 447 | 6/1999 |
| EP | 2 193 779 | 6/2010 |
| KR | 20050038312 A | 4/2005 |
| WO | 2005/016895 | 2/2005 |
| WO | 2008/101692 | 8/2008 |

OTHER PUBLICATIONS

Shim et al. "Selective Synthesis of N-(Cyclohexylmethyl)-N-alkylamines from Primary Amines and Pimelaldehyde using Tetracarbonylhydriodoferrate, HFe(CO)4, as a Reducing Reagent" Tetrahedron Letters, 1990, 31(1), 105-106.*
Hamada et al. "Photochemical Synthesis of 1,2,3,4-tetrahydroisoquinolin-3-ones and Oxindoles from N-chloroacetyl Derivatives of Benzylamines and Anilines. Role of Intramolecular Exciplex Formation and cis Conformation of Amide Bonds" Chem. Pharm. Bull. 1981, 29(1), 128-136.*
Thanigaimalai et al. "Evaluation of 3,4-dihydroquinazoline-2(1H)-thiones as inhibitors of a-MSH-induced melanin production in melanoma B16 cells" Bioorg. Med. Chem. 2010, 18, 1555-1562.*
Abstract of WO 2008/009860—published Jan. 24, 2008.
Abstract of DE 201 10 356—pubiished Aug. 30. 2001.
Abstract of WO 08/129188—published Oct. 30, 2008.
Araki, Jan. 1, 1983, Pharmacological Studies on Supersensitization, X Effect of Tripelennamine, Journal of Pharmacobio-Dynamics, vol. 6 No. 1, 1-8.
Fox, Jan. 1, 1951, N N-Substituted Ethylenediamine Derivatives, Journal of Organic Chemistry, vol. 16, 225-231.
PCT International Search Report in PCT appliction PCT/EP2011/059994 dated Feb. 23, 2012 with Written Opinion (U.S. Appl. No. 12/845,840).

* cited by examiner

*Primary Examiner* — Kortney L Klinkel
(74) *Attorney, Agent, or Firm* — Rimma Mitelman

(57) ABSTRACT

Skin care compositions comprising certain substituted monoamines, which are particularly beneficial for skin lightening and achieving evenness of color, especially for face and underarm skin.

7 Claims, No Drawings

SKIN CARE COMPOSITIONS COMPRISING SUBSTITUTED MONOAMINES

TECHNICAL FIELD

The present invention relates to compositions for face and body skin.

BACKGROUND OF THE INVENTION

The desire to look young and healthy is universal. The primary attributes of the young and healthy-looking skin are evenness of the skin color and texture. Age spots and other skin hyperpigmentation are undesirable. In many parts of the world, consumers also want to lighten their background skin color. Accordingly, there is a need for commercially feasible, effective skin care compositions, especially skin lightening products.

Various compositions comprising some substituted monoamines or related structures have been described, for example in EP 2193779 (Cognis); WO 2005/016895 (KIM); WO 2008/009860 (L'Oreal); Hirota et al., U.S. Pat. No. 4,412,943; EP 0653208 (Pfizer, Inc.); Dowell et al., U.S. Pat. No. 5,393,519; Winchell et al., US 2001/0041170; Chassot et al., US 2003/0172471; DE 20110356 (Wella AG); Walton, US 2005/0220832; Wagner et al., US 2009/0010860; WO 2008/101692 (Beiersdorf AG); WO 2008/129188 (L'Oreal); EP 0922 447 (Beiersdorf AG).

SUMMARY OF THE INVENTION

The present invention is based at least in part on the finding that among hundreds of compounds described as "substituted monoamines," a sub-group (Structure I below) with critical structural elements, is effective at inhibiting melanin production.

The invention includes skin care compositions, preferably skin lightening compositions, comprising substituted monoamines of Structure I. The invention also includes methods of using such compositions for skin care, especially face and underarms, most especially for skin lightening.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Skin Care Composition" as used herein, is meant to include a composition for topical application to skin of mammals, especially humans. Such a composition may be generally classified as leave-on or rinse off, and includes any product applied to a human body for improving appearance, cleansing, odor control or general aesthetics. The composition of the present invention can be in the form of a liquid, lotion, cream, foam, scrub, gel, soap bar or toner, or applied with an implement or via a face mask, pad or patch. Non-limiting examples of skin care compositions include leave-on skin lotions and creams, shampoos, conditioners, shower gels, toilet bars, antiperspirants, deodorants, dental products, shave creams, depilatories, lipsticks, foundations, mascara, sunless tanners and sunscreen lotions. "Skin" as used herein is meant to include skin on the face and body (e.g., neck, chest, back, arms, underarms, hands, legs, buttocks and scalp). The inventive compositions are especially useful for application to skin areas with the highest incidence of hyperpigmentation—face and underarms, most preferably the inventive compositions are skin lightening compositions, deodorants and anti-perspirants.

"Lightening" as used herein, means the lightening of skin color as well as the lightening of spots (hyperpigmentation) on the skin, like age spots and freckles.

Substituted Monoamines

The inventive compositions include substituted monoamines of Structure I:

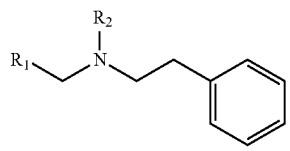

wherein $R_1$ is selected from the group consisting of cyclohexyl, phenyl, mono- and di-substituted phenyl with the following substituents: $C_1$-$C_5$ alkyl, $C_1$-$C_5$ alkoxy, phenoxy; and R2 is hydrogen or methyl. Preferably, to achieve improved inhibition of melanin production $R_1$ is mono- or di-substituted phenyl substituted, with one or two substitutions independently selected from the group consisting of hydrogen, methyl, ethyl, methoxy and phenoxy; and $R_2$ is selected from the group consisting of hydrogen and methyl.

It will be understood that Structure I also encompasses amine salts (e.g., halogen salts, tosylates, mesylates, carboxylates, and hydroxides).

Amounts of the substituted monoamines may range from 0.001% to 20%, preferably from 0.01 to 10%, more preferably from 0.1 to about 10%, optimally from 0.1 to about 5% by weight of the composition.

Process of Making Substituted Monoamines

Reagents & Analytical Methods

All reagents and solvents were obtained from commercial sources (Sigma-Aldrich, EMD Chemicals) and used without further purification unless otherwise indicated. Parallel reactions and parallel solvent removal were performed using a Buchi Syncore reactor (Buchi Corporation, New Castle, Del.). Reaction monitoring was performed using thin layer chromatography (TLC). TLC was performed using silica gel 60 $F_{254}$ plates (EMD Chemicals) and visualizing by UV (254 nm), 4% phosphomolybdic acid (PMA) in ethanol (EtOH), 4% ninhydrin in ethanol and/or using an iodine chamber. High performance liquid chromatography (HPLC) was performed using a Waters 2695 Separations Module equipped with a Waters 2996 Photodiode Array Detector and operated with Empower Pro software (Waters Corp.). Separations were carried out at 1 ml/min on a Restek Pinnacle DB C18 column (5 um, 4.6×150 mm) maintained at 30° C. Samples for HPLC were prepared by dissolving 1 mg of sample in 1 ml mobile phase A:B (1:1) and injecting 5 μL onto the column. The mobile phase consisted of A=0.1% trifluoroacetic acid (TFA) in water and B=0.1% TFA in acetonitrile (ACN) operated using gradient elution from 95:5 A:B to 5:95 A:B (gradient, 25 min) followed by 100% B (isocratic, 5 min). Liquid chromatography/mass spectrometry (LC-MS) was performed using a Finnigan Mat LCQ Mass Spectrometer via direct infusion of samples (50 ppm) in methanol and the total ion count monitored using electrospray ionization in the (+) mode (ESI+). $^1$H and $^{13}$C Nuclear magnetic resonance (NMR) spectroscopy was performed using a Eft-60 NMR Spectrometer (Anasazi instruments, Inc.) and processed using WinNuts software (Acorn NMR, Inc.). Melting points were determined using a Meltemp apparatus (Laboratory Devices). Purity was determined by HPLC-UV/Vis.

General Procedure: Synthesis of Substituted Monoamines (3)

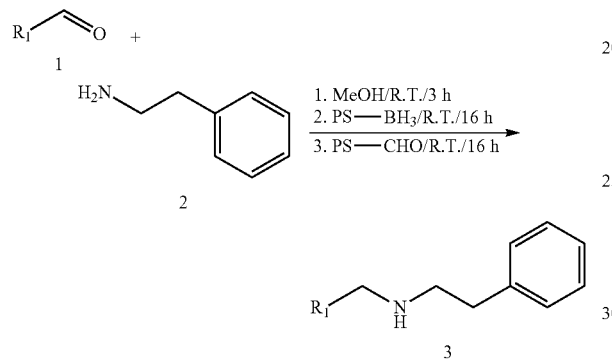

crude products were purified by flash chromatography on silica gel using the following (MeOH:CHCl$_3$) compositions: 3a, 3b, 3d, 3e, 3f (5:95); 3c, 3g (3:97). Product purity was determined by HPLC and product identity confirmed by LC-MS (ESI+).

Specific Procedures: Synthesis of Miscellaneous Compounds

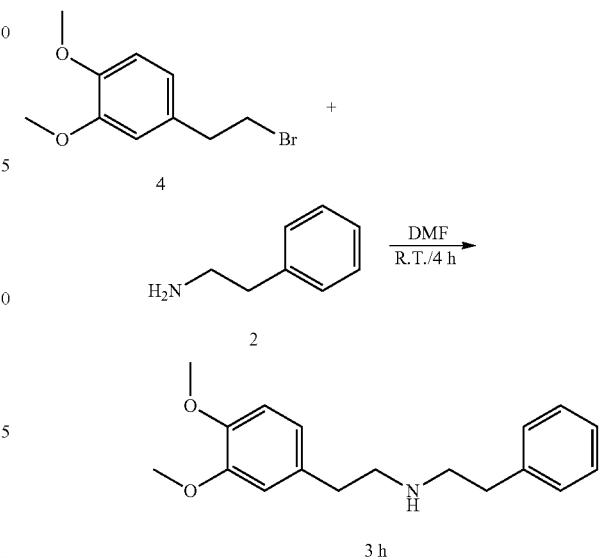

2-(3,4-dimethoxyphenyl)-N-phenethylethanamine (3h)-Phenethylamine 2 (222 mg, 1.83 mmol) was added to a solu-

| Structure ID | Chemical Name | R$_1$ | Purity (%) | LC-MS (% Relative Abundance) |
|---|---|---|---|---|
| 3a | N-(3,4-dimethoxybenzyl)-2-phenylethanamine | 3,4-dimethoxyphenyl | 99.5 | 272.1 (100) |
| 3b | N-(4-methoxybenzyl)-2-phenylethanamine | 4-methoxyphenyl | 94.3 | 242.0 (100) |
| 3c | N-(3-phenoxybenzyl)-2-phenylethanamine | 3-phenoxyphenyl | 99.5 | 304.1 (100) |
| 3d | N-(2,5-dimethoxybenzyl)-2-phenylethanamine | 2,5-dimethoxyphenyl | 99.1 | 272.1 (100) |
| 3e | N-(3,4-dimethylbenzyl)-2-phenylethanamine | 3,4-dimethylphenyl | 98.3 | 240.1 (100) |
| 3f | N-(cyclohexylmethyl)-2-phenylethanamine | cyclohexyl | 99.5 | 218.2 (100) |
| 3g | N-(3,5-dimethoxybenzyl)-2-phenylethanamine | 3,5-dimethoxyphenyl | 94.2 | 272.1 (100) |

Aldehydes 1 (1 mmol) were added to solutions of phenethylamine 2 (181 mg, 1.5 mmol) in methanol (MeOH) (2 mL) and the solutions stirred in a sealed vessel at room temperature for 3 h to allow for imine formation. Polystyrene borohydride resin (PS—BH$_3$) (1 g, 2.5 mmol) was added and the mixture stirred at room temperature (R.T.) for 16 h. The reactions were monitored by TLC using 5% methanol in chloroform (CHCl$_3$) and PMA staining until complete disappearance of the aldehydes. At this time, CHCl$_3$ (3 ml) was added, followed by polystyrene aldehyde resin (PS—CHO) (500 mg, 1.25 mmol) and the mixture stirred for 20 h. After complete disappearance of phenethylamine as monitored by TLC, the solids were filtered off and washed with methanol (5 ml) and the solvents removed under reduced pressure. The tion of 3,4-dimethoxyphenethylbromide 4 (300 mg, 1.22 mmol) in DMF (3 ml) and the solution stirred at R.T. for 4 h. At this time, TLC (5% methanol in chloroform) showed the complete disappearance of starting material and the formation of a major product. The solution was partitioned between t-butyl methyl ether (MTBE): 1N sodium hydroxide (NaOH) (10 ml: 7 ml), separated and the organic layer washed with saturated NaCl (10 ml), dried with Na$_2$SO$_4$ and the solvents removed to give an oil. The crude product was purified by flash chromatography using 5% methanol in chloroform. Identification of the desired product [m/z [M$_+$H]$^+$ 286.2 (100%)] was confirmed by LC-MS analysis (ESI+) and purity (99.4%) was confirmed by HPLC analysis ($\lambda_{max}$@272 nm).

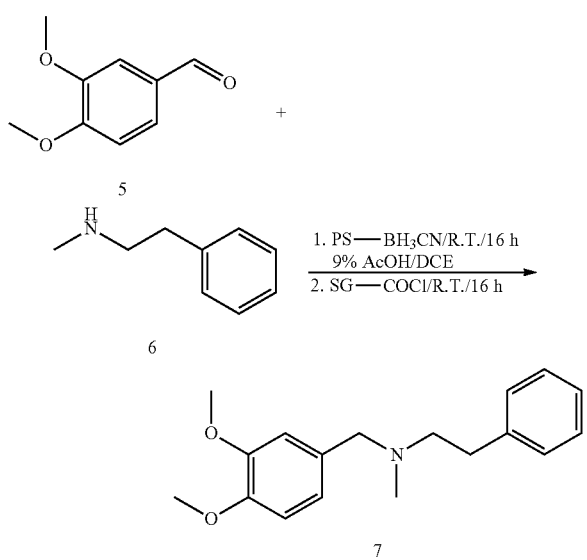

N-(3,4-dimethoxybenzyl)-N-methyl-2-phenylethanamine (7)—3,4-Dimethoxybenzaldehyde 5 (166 mg, 1 mmol) was added to a mixture of polystyrene cyanoborohydride resin (PS—BH₃CN) (1 g, 2.5 mmol) in 1,2-dichloroethylene (DCE) (3.7 ml), followed by N-methylphenethylamine 6 (203 mg, 1.5 mmol) and glacial acetic acid (AcOH) (370 µl) and the mixture stirred at R.T. for 16 h in a sealed vessel. At this time, TLC (5% methanol in chloroform) showed the clean formation of product. Silica gel-bound propionyl chloride (SG-COCl) (545 mg, 0.6 mmol) was added followed by DCE (3 ml) and the mixture stirred for 20 h. At this time, TLC showed the complete disappearance of N-methylphenethylamine. The solids were filtered off and washed with methanol (5 ml) and the solvents removed under reduced pressure. The crude product was purified by flash chromatography on silica gel using 3% MeOH in CHCl₃. Identification of the desired product [m/z [M+H]⁺ 286.2 (100%)] was confirmed by LC-MS analysis (ESI+) and purity (99.5%) was confirmed by HPLC analysis ($\lambda_{max}$@272 nm).

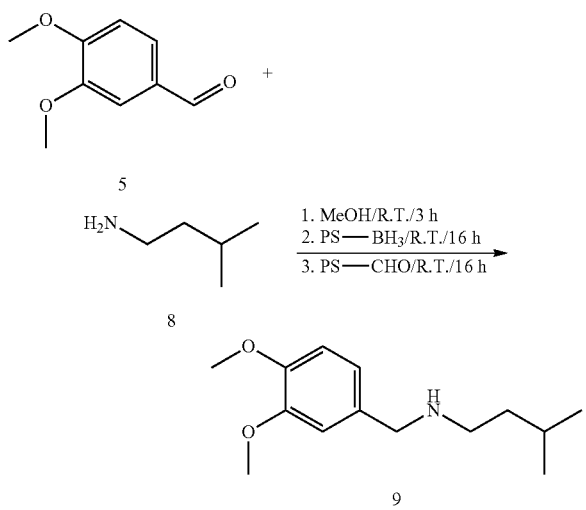

N-(3,4-dimethoxybenzyl)-3-methylbutan-1-amine (9)— Isopropylethylamine 8 (175 ul, 1.5 mmol) was added to a solution of 3,4-dimethoxybenzaldehyde 5 (166 mg, 1 mmol) in MeOH (2 ml) and the solution stirred in a sealed vessel at R.T. for 3 h to allow for imine formation. Polystyrene borohydride resin (1 g, 2.5 mmol) was added and the mixture stirred at R.T. for 16 h. At this time, TLC (5% methanol in chloroform) showed the clean formation of product. Polystyrene aldehyde resin (500 mg, 1.25 mmol) was added followed by CHCl₃ (3 ml) and the mixture stirred for 20 h. At this time, TLC showed very small amounts of isopropylethylamine. The solids were filtered off and washed with methanol (5 ml) and the solvents removed under reduced pressure. The crude product was purified by flash chromatography on silica gel using 8% MeOH in CHCl₃. Identification of the desired product [m/z [M+H]⁺ 238.0 (100%)] was confirmed by LC-MS analysis (ESI+) and purity (99.1%) was confirmed by HPLC analysis ($\lambda_{max}$@272 nm).

Skin Care Compositions

Compositions of this invention also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, humectants, thickeners and combinations thereof. The carrier may be aqueous, anhydrous or an emulsion. Preferably the compositions are aqueous, especially water and oil emulsions of the W/O or O/W or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m²/s at 25° C. Among the preferred nonvolatile emollients useful in the present compositions are the polydimethyl siloxanes having viscosities from about $1 \times 10^{-5}$ to about $4 \times 10^{-4}$ m²/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

1) Alkyl esters of saturated fatty acids having 10 to 24 carbon atoms. Examples thereof include behenyl neopentanoate, isononyl isonanonoate, isopropyl myristate and octyl stearate.

2) Ether-esters such as fatty acid esters of ethoxylated saturated fatty alcohols.

3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

4) Wax esters such as beeswax, spermaceti wax and tribehenin wax.

5) Sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol and cetyl alcohol.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, and silicates such as magnesium aluminum silicate (Veegum®). Amounts of the thickener may range from 0.0001 to 10%, usually from 0.001 to 1%, optimally from 0.01 to 0.5% by weight of the composition.

Optional Ingredients

The inventive composition preferably includes an additional skin lightening compound, to obtain optimum skin lightening performance at an optimum cost. Illustrative substances are placental extract, lactic acid, niacinamide, arbutin, kojic acid, ferulic acid, hydroquinone, resorcinol and derivatives including 4-substituted resorcinols and combinations thereof. More preferably, such additional skin lightening compound is a tyrosinase inhibitor, to complement the melanogenesis inhibition activity of the substituted monoamines, most preferably a compound selected from the group consisting of kojic acid, hydroquinone and 4-substituted resorcinol. Amounts of these agents may range from about 0.1 to about 10%, preferably from about 0.5 to about 2% by weight of the composition. It is preferred that the skin lightening coactive according to the invention is vitamin B3 or a derivative thereof and is selected from the group consisting of niacinamide, nicotinic acid esters, non-vasodilating esters of nicotinic acid, nicotinyl amino acids, nicotinyl alcohol esters of carboxylic acids, nicotinic acid N-oxide, niacinamide N-oxide and mixtures thereof.

Sunscreen is another preferred ingredient of the inventive compositions Particularly preferred are such materials as ethylhexyl p-methoxycinnamate (available as Parsol MCV®), Avobenzene (available as Parsol 1789®), octylsalicylate (available as Dermablock OS®), tetraphthalylidene dicamphor sulfonic acid (available as Mexoryl SX®), benzophenone-4 and benzophenone-3 (Oxybenzone). Inorganic sunscreen actives may be employed such as microfine titanium dioxide, zinc oxide, polyethylene and various other polymers. By the term "microfine" is meant particles of average size ranging from about 10 to about 200 nm, preferably from about 20 to about 100 nm. Amounts of the sunscreen agents when present may generally range from 0.1 to 30%, preferably from 2 to 20%, optimally from 4 to 10% by weight of the composition.

More preferred inventive compositions include both the additional skin lightening compound, especially tyrosinase inhibitor, and a sunscreen compound.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. Nos. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from or about 0.005% to or about 2%, more preferably 0.01% to or about 2%, retinoid. Retinol is preferably used in an amount of from or about 0.01% to or about 0.15%; retinol esters are preferably used in an amount of from or about 0.01% to or about 2% (e.g., about 1%); retinoic acids are preferably used in an amount of from or about 0.01% to or about 0.25%;

tocopheryl-retinoate, adapalene, and tazarotene are preferably used in an amount of from or about 0.01% to or about 2%.

Surfactants may also be present in compositions of the present invention. Total concentration of the surfactant when present may range from about 0.1 to about 40%, preferably from about 1 to about 20%, optimally from about 1 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionate, $C_8$-$C_{20}$ alkyl ether phosphates, $C_8$-$C_{20}$ sarcosinates and combinations thereof.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is pyridoxine palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001 to 10%, preferably from 0.01% to 1%, optimally from 0.1 to 0.5% by weight of the composition.

Another type of useful substance can be that of an enzyme such as oxidases, proteases, lipases and combinations. Particularly preferred is superoxide dismutase, commercially available as Biocell SOD from the Brooks Company, USA.

Desquamation promoters may be present. Illustrative are the monocarboxylic acids. Monocarboxylic acids may be substituted or unsubstituted with a carbon chain length of up to 16. Particularly preferred carboxylic acids are the alpha-hydroxycarboxylic acids, beta-hydroxycarboxylic or polyhydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic malic and tartaric acids. A representative salt that is particularly preferred is ammonium lactate Salicylic acid is representative of the beta-hydroxycarboxylic acids. Amounts of these materials when present may range from about 0.01 to about 15% by weight of the composition. Other phenolic acids include ferulic acid, salicylic acid, kojic acid and their salts.

Dicarboxylic acids represented by the formula HOOC-(CxHy)-COOH where x=4 to 20 and y=6 to 40 such as azelaic acid, sebacic acid, oxalic acid, succinic acid, fumaric acid, octadecenedioic acid or their salts or a mixture thereof.

A variety of herbal extracts may optionally be included in compositions of this invention. Illustrative are pomegranate, white birch (Betula Alba), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention may contain a safe and effective amount of a peptide active selected from pentapeptides, derivatives of pentapeptides, and mixtures thereof. As used herein, "pentapeptides" refers to both the naturally occurring pentapeptides and synthesized pentapeptides. Also useful herein are naturally occurring and commercially available compositions that contain pentapeptides. A preferred commercially available pentapeptide derivative-containing composition is Matrixyl®, which is commercially available from Sederma, France. The pentapeptides and/or pentapeptide derivatives are preferably included in amounts of from about 0.000001% to about 10%, more preferably from about 0.000001% to about 0.1%, even more preferably from about 0.00001% to about 0.01%, by weight of the composition. In embodiments wherein the pentapeptide-containing composition, Matrixyl®, is used, the resulting composition preferably contains from about 0.01% to about 50%, more preferably from about 0.05% to about 20%, and even more preferably from about 0.1% to about 10%, by weight of the resulting composition, of Matrixyl®.

Additional peptides, including but not limited to, di-, tri-, and tetrapeptides and derivatives thereof, and poly amino acid sequences of molecular weight from 200-20000. Amino acids may be naturally occurring or synthetic, dextro or levo, straight chain or cyclized and may be included in the compositions of the present invention in amounts that are safe and effective. As used herein, "peptides" refers to both the naturally occurring peptides and synthesized peptides. Also useful herein are naturally occurring and commercially available compositions that contain peptides.

Suitable dipeptides for use herein include Carnosine. Preferred tripeptides and derivatives thereof may be purchased as Biopeptide CL® and a copper derivative sold commercially as lamin, from Sigma (St. Louis, Mo.).

Skin moisturizers, e,g. hyaluronic acid and/or its precursor N-acetyl glucosamine may be included. N-acetyl glucosamine may be found in shark cartilage or shitake mushrooms and are available commercially from Maypro Industries, Inc (New York).

Anti-perspirants/deodorants skin care products of the invention may further include well known antiperspirant metal salts of aluminum, zinc, zirconium and zirconium aluminum mixtures of sulfates, chlorides, chlorohydroxides, tetrachlorohydrex glycinates, alums, formates, lactates, benzyl sulfonates, succinates, phenol sulfonates and the like. Typical levels of antiperspirant/deodorant agent are from about 0% to about 35%, preferably from about 0% to about 25% by weight of the composition. The composition may further include a complexing agent such as an organic acid or derivative thereof that are capable of forming complexes with the antiperspirant metallic salt. Examples of such complexing agents include, but are not limited to acetic acid, propionic acid, oxalic acid, malonic acid, succinic acid, tartaric acid, glycine and the like together with their cosmetically acceptable salts. Typical levels of complexing agent are from about 0% to about 15%, preferably from about 0% to about 10%, by weight of the composition.

The composition of the invention may comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition.

Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%.

Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C.

Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice are most often ethanol or sometimes iso-propanol. Polyhydric alcohols commonly comprise ethylene or propylene glycol, or a homologue can be employed such as diethylene glycol.

The compositions that remain in liquid form can be applied employing conventional applicators such as a roll-on or by being pumped or squeezed through a spray-generating orifice. Such compositions may be thickened, for example using one or more thickeners described subsequently herein.

Compositions that are firm solids, commonly obtained by use of a gellant or structurant, can be applied employing a stick applicator and soft solids, gels and creams can be applied employing an applicator having a dispensing head provided with at least one aperture through which the soft solid, gel or cream can be extruded under mild pressure.

Suitable thickeners or gellants that may be used for achieving this is by use of water-soluble or dispersible materials of higher viscosity, including various of the emulsifiers, and/or thickened or gelled with water-soluble or water-dispersible polymers including polyacrylates, and water-soluble or dispersible natural polymers, such as water-soluble polysaccharide or starch derivatives, such as alginates, carageenan, agarose and water-dispersible polymers include cellulose derivatives.

The concentration of such polymers in the water-immiscible liquid is often selected in the range of from 1 to 20%, depending on the extent of thickening or structuring required, and the effectiveness of the chosen polymer in the liquid/mixture.

One class of structurant which is desirable by virtue of its long standing proven capability to produce firm solids and more recently in making soft solids, comprises waxes. Herein, the term wax is employed to encompass not only materials of natural origin that are solid with a waxy feel and water-insoluble at 30-40° C., but melt at a somewhat higher temperature, typically between 50 and 95° C., such as beeswax, candelilla or carnauba wax, but also materials having similar properties. Such other waxes include hydrocarbon waxes, e.g. paraffin wax, mineral wax and microcrystalline wax; synthetic waxes, such as polyethylene of 2000 to 10000 daltons; waxy derivatives or waxy components of natural waxes Mixtures of materials within each class of gellant/structurant can be employed.

When the antiperspirant composition employed herein comprises an aerosol composition, it contains a propellant in addition to a base composition as described herein above, commonly in a weight ratio of from 95:5 to 40:60, and in many formulations, the weight ratio is from 90:10 to 50:50.

The propellant is conveniently a low boiling point material, typically boiling below −5° C., for example an alkane such as propane, butane or isobutane, and possibly containing a fraction of pentane or isopentane, or a hydrofluorocarbon or fluorocarbon of similar carbon content. During filling of the aerosol canister, the propellant gas is liquified by virtue of the elevated pressure that is generated therein.

Examples of a hardening agent useful in the skin care compositions of the present invention include, but are not limited to lower alkanol amines, diamines and amides wherein such materials comprise at least two lower alkanol groups, preferably from about two to about four lower alkanol groups having from about 2 to about 4 carbon atoms. Examples of such hardening agents include, but are not limited to tetrahydroxyalkyldiamine compounds such as tetrahydroxypropylethylenediamine, polyoxamine compounds such as polyoxyethylene, polyoxypropylene block copolymers of ethylenediamine and alkanolamide compounds such as coconut diethanolamide and lauryl monoethanolamide. Typical levels of hardening agent are from about 0% to about 5% by weight of the composition.

Further ingredients useful in skin care compositions herein may be selected from any and all: skin conditioning agents, skin feel mildness agents, suspending agents, auxiliary thickening agents, viscosity control agents, dispersants, solubilizing/clarifying agents, stabilizers, opacifiers/pearlescent agents, chelating/sequestering agents, hydrotropes, bactericides/fungicides, antioxidants, pH control agents, buffering agents, colorants and perfumes/fragrances, water, other optional ingredients (auxilary agents) and the like.

The compositions of the present invention can also be optionally, incorporated into a water insoluble substrate for application to the skin such as in the form of a treated wipe.

While the above summarizes the present invention, it will become apparent to those skilled in the art that modifications, variations and alterations may be made without deviating from the scope and spirit of the present invention as described and claimed herein. The invention will now be further illustrated in the following non-limiting examples.

EXAMPLE 1

Various representative substituted monoamines of Structure I within the scope of the invention were investigated for inhibition of melanogenesis activity.

Melanoderm tissue equivalent model MEL-300 (MatTek: Ashland, Mass.) containing melanocytes obtained from dark skin individuals were cultured as per supplier instructions. Components were added to the maintenance medium phase (no topical treatments) at a final concentration of 10 μM for 14 days at which time the experiment was terminated and the tissues assessed for melanin content. Medium and treatments were changed three times per week. DMSO was utilized as the vehicle control and all treatments were performed at least in duplicate.

For quantification of total melanin, each Melanoderm was placed into an individual Eppendorf tube (2 mL) into which 250 μL of Solvable™ tissue solubilizer (Packard Bioscience Co., Cat #6NE9100) was added. Each tube was vortexed and incubated at 60° C. for 18 hours. Each sample was then centrifuged (5-minutes at 13,000 RPMs) to remove any particulates. 100 or 200 μL of supernatant were transferred to a 96 well microtiter plate and the absorbance read at 490 nm. Total melanin content was calculated from a standard curve using synthetic melanin (Sigma Cat #M8631). Data was analyzed for significance using the t-test in Microsoft Excel to generate p-values (p-values less than 0.01 represent 99% confidence, p values of 0.05 represent 95% confidence both of which are statistically significant).

The results that were obtained are summarized in Table 1. The results show that compounds included in this invention inhibit melanogenesis.

TABLE 1

| Compound ID | Structure | Melanoderm (% Reduction at 10 μM) | p value |
|---|---|---|---|
| 3a | 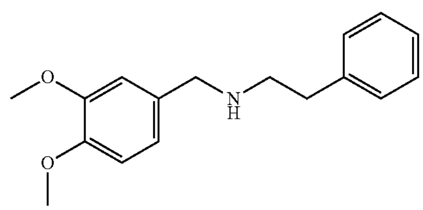 | 40.3 | 0.0116 |
| 3b | 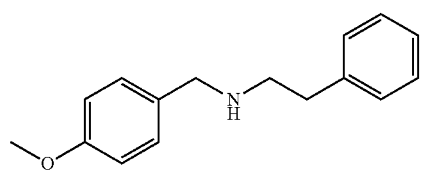 | 54.4 | 0.0065 |
| 3c | 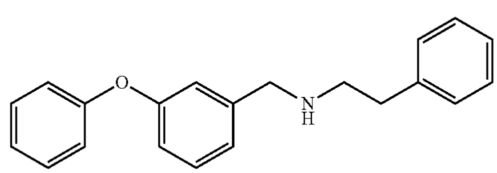 | 68.9 | 0.0040 |
| 3d | 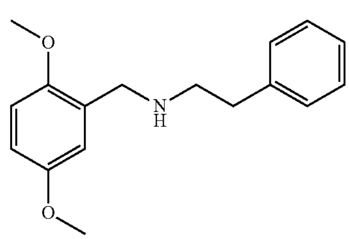 | 60.3 | 0.0051 |
| 3e | 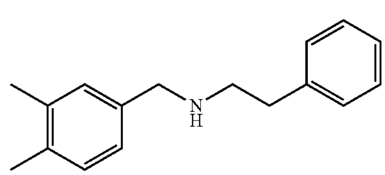 | 64.5 | 0.0046 |

TABLE 1-continued

| Compound ID | Structure | Melanoderm (% Reduction at 10 μM) | p value |
|---|---|---|---|
| 3f | 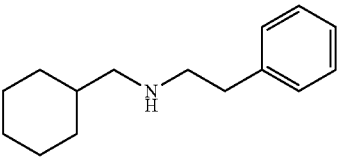 | 69.5 | 0.0040 |
| 3g | 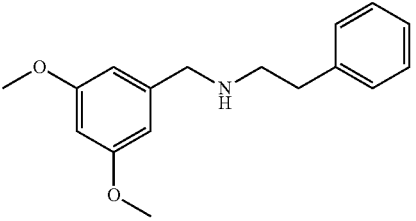 | 51.6 | 0.0069 |
| 3h | 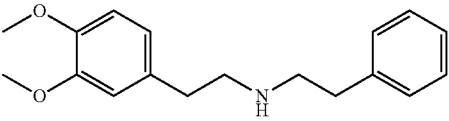 | 53.1 | 0.0066 |
| 7 | 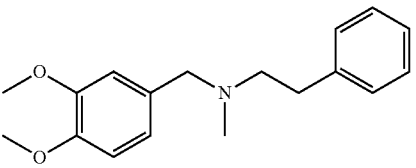 | 44.4 | 0.0096 |

COMPARATIVE EXAMPLE 2

This example investigated structural criticalities of the compounds within the invention.

| Compound ID | Structure | Melanoderm (% Reduction at 10 μM) | p value |
|---|---|---|---|
| 9 | 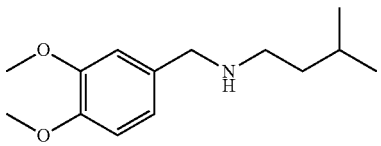 | 1.9 | 0.4510 |

It can be seen from comparing Compound 3a in Table 1 (within the scope of the invention) to Compound 9 in Example 2 (outside the scope of the invention) that the terminal phenyl ring is critical for inhibition of melanogenesis activity.

EXAMPLE 3

The following skin lightening product is prepared according to the invention:

| INGREDIENT | % composition by weight |
|---|---|
| Water | q.s. to 100 |
| Stearic acid | 18.00 |
| Cetyl alcohol | 0.40 |
| Glyceryl monostearate | 0.60 |
| Silicone oil | 0.50 |
| Sodium cetostearyl sulphate | 1.0 |
| Mixture of sorbitan esters and ethoxylated fatty acid esters | 1.5 |
| Alkyl acrylate cross polymer | 0.15 |
| Polyhydric alcohol | 10.00 |
| Preservatives | 0.5 |

| INGREDIENT | % composition by weight |
| --- | --- |
| Niacinamide | 1.00 |
| Inventive compound 3f | 2.00 |
| Parsol MCX | 0.4 |
| Benzophenones | 0.75 |
| Titanium dioxide | 0.6 |

EXAMPLE 4

Skin care products within the scope of the invention are prepared:

| Component | A | B | C | D |
| --- | --- | --- | --- | --- |
| Disodium EDTA | 0.100 | 0.100 | 0.100 | 01.00 |
| Inventive Compound 3f | 2.000 | 0 | 1 | 0 |
| Inventive Compound 3b | 0 | 2.000 | 0 | 1 |
| Methyl sulfonyl methane | 0 | 0 | 2.000 | 0 |
| Niacinamide | 4.000 | 4.000 | 4.000 | 5.000 |
| Octadecenedioic acid | 0 | 0 | 0 | 2.000 |
| Isohexadecane | 3.000 | 3.000 | 3.000 | 3.000 |
| Isopropyl isostearate | 1.330 | 1.330 | 1.330 | 1.330 |
| Sucrose polycottonseedate | 0.670 | 0.670 | 0.670 | 0.670 |
| Polymethylsilsesquioxane | 0.250 | 0.250 | 0.250 | 0.250 |
| Cetearyl glucoside + cetearyl alcohol | 0.200 | 0.200 | 0.200 | 0.200 |
| Behenyl alcohol | 0.400 | 0.400 | 0.400 | 0.400 |
| Ethylparaben | 0.200 | 0.200 | 0.200 | 0.200 |
| Propylparaben | 0.100 | 0.100 | 0.100 | 0.100 |
| Cetyl alcohol | 0.320 | 0.320 | 0.320 | 0.320 |
| Stearyl alcohol | 0.480 | 0.480 | 0.480 | 0.480 |
| Tocopheryl acetate | 0.500 | 0.500 | 0.500 | 0.500 |
| PEG-100 stearate | 0.100 | 0.100 | 0.100 | 0.100 |
| Glycerin | 7.000 | 7.000 | 7.000 | 10.000 |
| Titanium dioxide | 0.604 | 0.604 | 0.604 | 0.604 |
| Polyacrylamide + C13-14 isoparaffin + laureth-7 | 2.000 | 2.000 | 2.000 | 2.000 |
| Panethenol | 1.000 | 1.000 | 1.000 | 1.000 |
| Benzyl alcohol | 0.400 | 0.400 | 0.400 | 0.400 |
| Dimethicone + dimethiconol | 2.000 | 2.000 | 2.000 | 2.000 |
| Water (to 100 g) | to 100 | to 100 | to 100 | To 100 |
| Total | 100 | 100 | 100 | 100 |

The water phase ingredients were combined in a suitable vessel and heated to 75° C. In a separate suitable vessel, combine the oil phase ingredients and heat to 75° C. Next add the oil phase to the water phase and mill the resulting emulsion (e.g., with a Tekmar™ T-25 mill). Then, add the thickener to the emulsion and cool the emulsion to 45° C. while stirring. At 45° C., add the remaining ingredients. Cool the product and stir to 30° C. and pour into suitable containers. The compositions are chronically applied topically to areas of hyperpigmented skin.

EXAMPLE 5

A representative skin care composition of the present invention in the form of a cosmetic lotion is outlined below:

| INGREDIENT | WEIGHT % |
| --- | --- |
| Water | Balance |
| Disodium EDTA | 0.05 |
| Methyl Paraben | 0.15 |
| Magnesium Aluminum Silicate | 0.60 |
| Triethanolamine | 1.20 |
| Inventive compound 3f | 1.00 |
| Xanthan Gum | 0.20 |
| Natrosol ® 250HHR (ethyl cellulose) | 0.50 |
| Butylene Glycol | 3.00 |
| Glycerin | 2.00 |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearin Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| (Isotridecyloxy)propionic acid (branched) or (Isotridecyloxy)acetic acid (branched) | 2.00 |
| Vitamin A Palmitate | 0.10 |
| Bisabolol | 0.01 |
| Vitamin A Acetate | 0.01 |
| Fragrance (20% Limonene and 3% gamma terpinene) | 0.03 |
| Retinol 50C | 0.02 |

EXAMPLE 6

A water-in-oil topical liquid make-up foundation according to invention is described:

| INGREDIENT | WEIGHT % |
| --- | --- |
| (Isotridecyloxy)propionic acid (branched) or (Isotridecyloxy)acetic acid (branched) | 2.00 |
| Cyclomethicone | 9.25 |
| Oleyl Oleate | 2.00 |
| Dimethicone Copolyol | 20.00 |
| Talc | 3.38 |
| Pigment (Iron Oxides) | 10.51 |
| Spheron L-1500 (Silica) | 0.50 |
| Synthetic Wax Durachem 0602 | 0.10 |
| Arachidyl Behenate | 0.30 |
| Cyclomethicone | 1.00 |
| Trihydroxystearin | 0.30 |
| Laureth-7 | 0.50 |
| Propyl Paraben | 0.25 |
| Perfume | 0.1 |
| Water | balance |
| Inventive compound 3b | 3.00 |
| Methyl Paraben | 0.12 |
| Propylene Glycol | 8.00 |
| Niacinamide | 4.00 |
| Glycerin | 3.00 |
| Sodium Chloride | 2.00 |
| Sodium Dehydroacetate | 0.30 |

EXAMPLE 7

An aerosol packaged foaming cleanser is outlined:

| INGREDIENT | WEIGHT % |
| --- | --- |
| Sunflower Seed Oil | 10.00 |
| Glycerin | 10.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Inventive compound 3f | 1.00 |
| Fragrance (20% Limonene) | 1.00 |
| Water | Balance |

EXAMPLE 8

A toilet bar illustrative of the present invention is outlined:

| INGREDIENT | WEIGHT % |
| --- | --- |
| Sodium Soap (85/15 Tallow/Coconut) | 77.77 |
| Inventive compound 3e | 3.50 |
| Dimethicone | 2.00 |
| Sodium Chloride | 0.77 |
| Titanium Dioxide | 0.40 |
| Ethylene Brassylate | 1.50 |
| Disodium EDTA | 0.02 |
| Sodium Etidronate | 0.02 |
| Fluorescer | 0.024 |
| Water | Balance |

EXAMPLE 9

A shampoo composition useful in the context of the present invention is described:

| INGREDIENT | WEIGHT % |
| --- | --- |
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Glycerin | 12.00 |
| Inventive Compound 7 | 5.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance (10% Limonene) | 0.40 |
| Sodium Benzoate | 0.25 |
| Kathon CG ® | 0.0008 |
| Benzyl Alcohol | 0.0225 |
| Water | Balance |

EXAMPLE 10

This Example illustrates an antiperspirant/deodorant formula incorporating the substituted monoamine compound according to the present invention.

| Ingredient | Weight % |
| --- | --- |
| (Isotridecyloxy)propionic acid (branched) | 2.00 |
| Cyclopentasiloxane | 39 |
| Dimethicone | 20 |
| Aluminum Zirconium Trichlorohydrex Glycinate | 15 |
| Inventive Compound 7 | 5.0 |
| C18-C36 Acid Triglyceride | 5.0 |
| Microcrystalline Wax | 3.0 |
| Glycerin | 8.0 |
| Silica | 2.5 |
| Dimethicone Crosspolymer | 1.0 |
| Ethylene Brassylate | 0.5 |
| Disodium EDTA | 0.4 |
| Butylated Hydroxytoluene | 0.3 |
| Citric Acid | 0.3 |

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

What is claimed is:

1. A skin lightening water and oil emulsion comprising:
   (a) from about 0.001% to about 20% of a substituted monoamine of structure I:

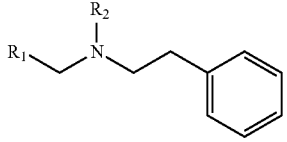

I wherein $R_1$ is selected from the group consisting of cyclohexyl, phenyl, mono- and di-substituted phenyl wherein the mono- and di-substitutions are independently selected from the group consisting of: $C_1$-$C_5$ alkyl, $C_1$-$C_5$ alkoxy, and phenoxy; and $R_2$ is selected from the group consisting of hydrogen and methyl;
   (b) an additional skin lightening active selected from the group consisting of placental extract, lactic acid, niacinamide, arbutin, kojic acid, ferulic acid, hydroxyquinone, resorcinol and 4-substituted resorcinols, and
   (c) a cosmetically acceptable carrier selected from the group consisting of water, emollients, fatty acids, fatty alcohols, humectants, thickeners and combinations thereof.

2. The composition of claim 1, wherein $R_1$ is mono- or di-substituted phenyl wherein the mono- and di-substitutions are independently selected from the group consisting of methyl, ethyl, methoxy, and phenoxy; and $R_2$ is selected from the group consisting of hydrogen and methyl.

3. The composition of claim 1, wherein $R_2$ is hydrogen.

4. The composition of claim 1 further comprising an ingredient selected from the group consisting of alpha-hydroxy acids, beta-hydroxyacids, tyrosinase inhibitors, organic sunscreens, inorganic sunscreens, vitamins, retinol, retinyl esters, peptides, N-acetylglucosamines, anti-inflammatories, and anti-oxidants.

5. The composition of claim 1 further comprising an antiperspirant active.

6. The composition of claim 1 further comprising a surfactant.

7. A method of lightening skin, the method comprising applying to the skin the composition of claim 1.

* * * * *